(12) United States Patent
Meyer et al.

(10) Patent No.: US 9,594,072 B2
(45) Date of Patent: Mar. 14, 2017

(54) SYSTEM AND METHOD FOR DETERMINING CELL ADEQUACY IN A CYTOLOGICAL ANALYSIS SYSTEM

(71) Applicant: VISIONGATE, INC., Phoenix, AZ (US)

(72) Inventors: Michael G. Meyer, Phoenix, AZ (US); Rahul Katdare, Tempe, WA (US); Chris Presley, Phoenix, AZ (US); Timothy Bell, Phoenix, AZ (US)

(73) Assignee: VISIONGATE, INC., Phoenix, AZ (US)

( * ) Notice: Subject to any disclaimer, the term of this patent is extended or adjusted under 35 U.S.C. 154(b) by 0 days.

(21) Appl. No.: 14/788,015

(22) Filed: Jun. 30, 2015

(65) Prior Publication Data

US 2017/0003267 A1    Jan. 5, 2017

(51) Int. Cl.
*G01N 33/483*    (2006.01)

(52) U.S. Cl.
CPC ................................ *G01N 33/4833* (2013.01)

(58) Field of Classification Search
CPC ............. G01N 21/4975; G01N 5/1475; G01N 15/147; G01N 2015/1445; G01N 2021/1787; G06T 11/005; G06T 11/008; G06T 2200/04; G06T 2207/10072; G06T 2207/10101; G06K 9/00127; G06K 9/00147; A61B 5/0073
See application file for complete search history.

(56) References Cited

U.S. PATENT DOCUMENTS

| 5,799,101 | A | * | 8/1998 | Lee | ....................... G06K 9/6282 128/922 |
| 5,978,497 | A | * | 11/1999 | Lee | ..................... G01N 15/1475 382/133 |
| 6,522,775 | B2 | | 2/2003 | Nelson | |
| 7,738,945 | B2 | | 6/2010 | Fauver et al. | |
| 7,835,561 | B2 | | 11/2010 | Meyer et al. | |
| 7,907,765 | B2 | | 3/2011 | Fauver et al. | |
| 8,155,420 | B2 | | 4/2012 | Meyer et al. | |
| 8,254,023 | B2 | | 8/2012 | Watson et al. | |
| 2010/0296713 | A1 | * | 11/2010 | Meyer | ................ G06K 9/00147 382/131 |
| 2012/0191635 | A1 | * | 7/2012 | Bigio | ................... A61B 5/0059 706/13 |

(Continued)

*Primary Examiner* — Edward Park
(74) *Attorney, Agent, or Firm* — George A. Leone; Citadel Patent Law (57) ABSTRACT

A cytological analysis test for 3D cell classification from a specimen. The method includes isolating and preserving a cell from the specimen and enriching the cell before embedding the enriched cell into an optical medium. The embedded cell is injected into a capillary tube where pressure is applied until the cell appears in a field of view of a pseudo-projection viewing subsystem to acquire a pseudo-projection image. The capillary tube rotates about a tube axis to provide a set of pseudo-projection images for each embedded cell which are reconstructed to produce a set of 3D cell reconstructions. Reference cells are classified and enumerated and a second cell classifier detects target cells. An adequacy classifier compares the number of reference cells against a threshold value of enumerated reference cells to determine specimen adequacy.

27 Claims, 7 Drawing Sheets

(56) References Cited

U.S. PATENT DOCUMENTS

| | | | | |
|---|---|---|---|---|
| 2014/0119630 A1* | 5/2014 | Sowards-Emmerd | . | A61B 6/032 382/131 |
| 2014/0296089 A1* | 10/2014 | Holmes | ............... | G01N 35/026 506/9 |
| 2015/0104786 A1* | 4/2015 | Shirasuna | ............ | C12Q 1/6886 435/6.1 |

* cited by examiner

SYSTEM AND METHOD FOR DETERMINING CELL ADEQUACY IN A CYTOLOGICAL ANALYSIS SYSTEM

TECHNICAL FIELD

The present invention relates to optical tomography on a cellular and sub-cellular scale. More particularly, the invention relates to a system and method for determining the adequacy of a sample analyzed by a cancer detection test system.

BACKGROUND

Lung cancer is the second most prevalent cancer in the United States and is the most lethal[4]. Over 31 million patients in the United States (US) are at high risk for the development of lung cancer, primarily due to a smoking history. Approximately 160,000 US patients die of lung cancer each year[4]. Many attempts have been made to develop screening procedures for lung cancer. Traditional cytological methods based on sputum or bronchial wash specimens have been shown to be relatively insensitive, with only about 40-60% of patients with cancer having positive results and the majority of those being from endobronchial squamous carcinomas[5, 8, 7]. One bright spot related to the cytology examination is the relatively high positive predictive value of this procedure—generally above 98% —meaning that a positive test is a reliable indicator of disease[7].

The Centers for Medicare/Medicaid Services (CMS) has recently approved reimbursement coverage for low dose CT radiographic scanning (LDCT) for lung cancer screening in highest risk patients[8], and the US Preventive Services Task Force and a number of other professional and advocacy organizations have made recommendations for screening in high risk populations[9,10]. Results of the National lung Cancer Screening Trial showed that the use of LDCT can decrease the mortality from lung cancer by 20% compared to conventional chest x-ray[10]. Although sensitive for the detection of pulmonary neoplasia (after three consecutive LDCT scans), LDCT has low specificity with false positive results in as high as 96% of patients with a nodule, leading to low positive predictive values[11]. In addition, the cost and morbidity/mortality associated with continued surveillance and interventional follow-up must be accounted for, particularly in the false positive population[12]. The addition of a non-invasive triage test (such as an early lung cancer detection test) with much higher specificity, therefore, has potential in managing patients who test positive with LDCT examinations. In addition, if the test's sensitivity is also high, then it has the potential to be useful as an independent primary lung cancer screening test as well.

In a related technology, automated and semi-automated algorithmic classifiers based on 2-dimensional morphologic parameters have been in wide clinical use since the 1990's for cervical cytology specimens. One such device is now being marketed as the FocalPoint Primary Screening System (Becton-Dickinson, Franklin Lakes, N.J.[1, 2]. The classifiers of the FocalPoint were trained on human evaluation of cells in a labelling process which then informed the algorithmic classifiers, allowing newly presented cells (and cases) to be given probabilities of abnormality. Individual cells and/or cases falling above designated score thresholds are at much higher risk for being abnormal than are those falling below the threshold and can therefore be selected on that basis for focused review by cytologists[1, 2].

Extension of this concept to 3-dimensional morphometric analysis provides the potential for a significantly greater number of measured parameters that are statistically robust and, hence, improve accuracy and clinical performance. Three-dimensional analysis provides much higher resolution of cellular and sub-cellular intricacies than can the currently used cytology devices[3]. Given the high morbidity of lung cancer, there is a need for a lung cancer detection test for the detection of lung cancer in its early stages. Such a lung cancer detection test has both the potential for use as a primary screener for lung cancer and also as a test to use adjunctively with LDCT to reduce false positives and costs of screening by LDCT alone.

In pursuit of such an early lung cancer detection system, advances in 3D imaging of biological cells using optical tomography have been developed by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further major developments in the field are taught in Fauver et al., U.S. Pat. No. 7,738,945, issued Jun. 15, 2010, entitled "Method and Apparatus for Pseudo-projection Formation for Optical Tomography," (Fauver '945) and Fauver et al., U.S. Pat. No. 7,907,765, issued Mar. 15, 2011, entitled "Focal Plane Tracking for Optical Microtomography," (Fauver '765) the full disclosures of Fauver '945 and Fauver '765 are also incorporated by reference. Building on the teachings therein an early lung cancer detection technology has been developed by VisionGate, Inc., Phoenix, Ariz. to provide measurement advantages that have the potential to greatly improve the operating characteristics of conventional morphologic cytology analyses. New systems and methods related to such an early lung cancer detection test are described herein.

Processing in such an optical tomography system begins with specimen preparation. Typically, specimens taken from a patient are received from a hospital or clinic and processed to remove non-diagnostic elements, fixed and then stained. Stained specimens are then mixed with an optical gel, inserted into a microcapillary tube. Images of objects, such as cells, in the specimen are produced using an optical tomography system. The resultant images comprise a set of extended depth of field images from differing perspectives called "pseudo-projection images." The set of pseudo-projection images can be reconstructed using backprojection and filtering techniques to yield a 3D reconstruction of a cell of interest. Having isometric or roughly equal resolution in all three dimensions is an advantage in 3D tomographic cell imaging, especially for quantitative image analysis.

The 3D reconstruction then remains available for analysis in order to enable the quantification and the determination of the location of structures, molecules or molecular probes of interest. An object such as a biological cell may be labeled with at least one stain or tagged molecular probe, and the measured amount and location of this biomarker may yield important information about the disease state of the cell, including, but not limited to, various cancers such as lung, breast, prostate, cervical, stomach and pancreatic cancers.

Unfortunately, currently available testing techniques are hampered by the lack of a method to determine if the specimen has been sufficiently analyzed. In the present invention it has been discovered that, since tumor or abnormal cells shed from the epithelium of a given organ system along with normal cells, these normal cells provide an excellent marker to determine if the specimen has been sufficiently sampled. Using the novel techniques disclosed herein, specimens meeting these conditions are determined to be adequate specimens.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A cytological analysis test for 3D cell classification from a specimen is disclosed. The method includes isolating and preserving a cell from the specimen, and enriching the cell before embedding the enriched cell into an optical medium. The embedded cell is injected into a capillary tube where pressure is applied until the cell appears in a field of view of a pseudo-projection viewing subsystem to acquire a pseudo-projection image. The capillary tube rotates about a tube axis to provide a set of pseudo-projection images for each embedded cell which are reconstructed to produce a set of 3D cell reconstructions. Reference cells are classified and enumerated and a second cell classifier detects target cells. An adequacy classifier compares the number of reference cells against a threshold value of enumerated reference cells to determine specimen adequacy.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements, and have been solely selected for ease of recognition in the drawings.

DETAILED DESCRIPTION OF THE PREFERRED EMBODIMENTS

The following disclosure describes a specimen adequacy classifier for use in cancer analysis. Several features of methods and systems in accordance with example embodiments are set forth and described in the figures. It will be appreciated that methods and systems in accordance with other example embodiments can include additional procedures or features different than those shown in the figures. Example embodiments are described herein with respect to an optical tomography cell imaging system. However, it will be understood that these examples are for the purpose of illustrating the principles, and that the invention is not so limited.

The present invention provides an early lung cancer detection system using specimens including patient sputum which is processed by an optical tomography system that produces isometric, sub-micron resolution 3D cell images that are then interrogated by automated feature extraction and classification algorithms to identify abnormal cells in sputum with high accuracy. Since abnormal cells are rare in sputum and non-diagnostic contaminants are plentiful, only a system capable of cell detection with high sensitivity and very high specificity can manage the lung cancer detection in sputum in an efficient way while assuring specimen adequacy.

There are many potential uses of the presently disclosed optical tomography system; the most advantageous being in specimens that have low yields of neoplastic cells or in which the abnormal cells are difficult to recognize when compared to the background of non-neoplastic cells. Examples include the detection of circulating tumor cells in blood and neoplastic cells in sputum in cases of early or peripheral lung cancer. It is the latter application that this preliminary study investigates.

DEFINITIONS

Generally, as used herein, the following terms have the following meanings: The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Capillary tube" has its generally accepted meaning and is intended to include transparent microcapillary tubes and equivalent items with an inside diameter generally of 500 microns or less.

"Cell-CT® platform" refers to an optical tomography system manufactured by VisionGate, Inc. of Phoenix, Ariz.

incorporating teachings of the Nelson and Fauver patents referenced herein above and improvements of those teachings.

"Depth of field" is the length along the optical axis within which the focal plane may be shifted before an unacceptable image blur for a specified feature is produced.

"LuCED® test" refers to an early lung cancer test employing the Cell-CT® platform as developed by VisionGate, Inc. of Phoenix, Ariz. incorporating the teachings of the Nelson and Fauver patents referenced hereinabove and improvements of those teachings.

"Object" means an individual cell, item, thing or other entity.

"Pseudo-projection" includes a single image representing a sampled volume of extent larger than the native depth of field of the optics where pseudo-projection image thus formed include an integration of a range of focal plane images from a fixed viewpoint. The concept of a pseudo-projection is taught in Fauver '945.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

"Threshold" as used in the context of image processing includes a decision boundary value for any measurable characteristic of a feature. Thresholds may be predetermined or set according to instrument specifications, acceptable error rates, statistics, or other criteria according to accepted pattern recognition principles.

"Voxel" as used in the context of image processing is a volume element on a 3D grid.

Overview

Figure 1:
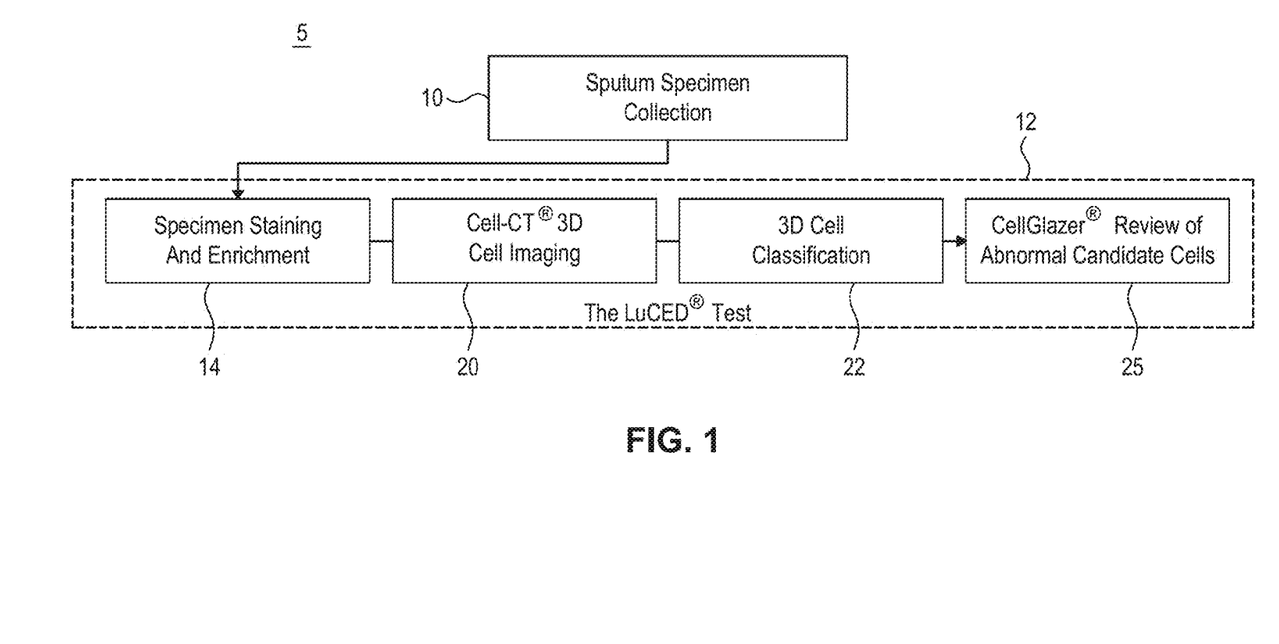
FIG. 1 schematically shows a functional overview of a lung cancer test for analysis of a sputum sample.

Referring to FIG. 1, a functional overview of a lung cancer test system for analysis of a sputum sample is schematically shown. The test system 5 includes apparatus and methods for sputum specimen collection 10 followed by a test for early lung cancer detection 12 such as, for example, the LuCED® test. The early lung cancer test 12 further includes an apparatus and methods for specimen staining and enrichment 14, 3D cell imaging 20, 3D cell classification 22 and clinician review of abnormal candidate cells 25.

Sputum collection is typically done through spontaneous coughs in the patient's home or through induction in a clinic. Sputum is processed to remove contaminants and non-bronchial epithelial cells as, for example, by de-bulking the white cells and oral squamous cells. The enriched specimen is processed on the Cell-CT® platform that images cells digitally in true 3D with isometric, sub-micron resolution as disclosed, for example in Nelson and Fauver referenced above. The bio-signatures associated with cancer are measured on the 3D cell images and combined into a score that is used to identify those few cells that have cancer characteristics. These cells are then displayed for manual cytologist review using a review station such as a CellGazer™ review station as developed by VisionGate, Inc., Phoenix, Ariz. The review station provides visual displays allowing a cytologist to view cell images in 2D and 3D to establish a definitive normal or abnormal status for specific cell candidates. Three-dimensional (3D) cell classification 22 may be carried out using techniques as disclosed herein below.

The cell imaging system 20 includes a process implemented through computer software executed, for example, by a personal computer interfacing with opto-mechanical devices to correct for motion arising during image capture. Most cell images emerge from filtered back-projection in a well-reconstructed way. This algorithm identifies cells that were poorly reconstructed so they can be rejected from further processing. One example of a method for detecting poor quality reconstructions is taught by Meyer et al. in U.S. Pat. No. 8,155,420, issued Apr. 10, 2012 and entitled "System and Method for Detecting Poor Quality in 3D Reconstructions," the disclosure of which is incorporated herein by reference.

Earlier attempts at the development of a lung cancer-screening program were based on sputum cytology[7] which showed an insufficient sensitivity to disease detection (about 60% on average) but with very good specificity. This experience led some to conclude that sputum is not valuable for detection of lung cancer. A careful analysis involving sputum embedded in paraffin blocks showed that the specimen actually contains abnormal cells in 86% of cancer patients [8]. Collection by morning coughs over three successive days yielded optimal results. A further analysis showed that abnormal cells are present in sputum stratified by all relevant clinical factors, including tumor histologic type, size, stage and location[9]. Based on these specimen characteristics, the presently disclosed lung cancer detection test employs spontaneous cough sputum. Initial evaluations have shown satisfactory results using sputum fixation by either Cytoyt (Hologic, Marlborough, Mass.) or the well-known Saccomanno's method. The question of specimen adequacy is also important for sputum cytology. Attempts at increasing the volume of the sputum expectorate have met with varied success. Sputum induction[10, 11] increases production of phlegm to help achieve an overall adequate sample.

Examples of Sputum Enrichment and Preparation In one example of a lung cancer detection test, sputum specimens undergo three stages of processing prior to analysis: 1) Sputum cell isolation and cryopreservation; 2) enrichment by fluorescence activated cell sorting (FACS); and 3) embedding of enriched cells into optical oil that is index-matched to the optical components of the optical tomography imaging system.

Cryopreservation and FACS Enrichment

Sputum is treated with the mucolytic agent dithiothreitol (DTT) (Fisher Scientific, Waltham, Mass.). For longer term storage, the specimen is then filtered through a 41 μm nylon net and kept at −80° C. in 15% dimethyl sulfoxide (DMSO) (Fisher Scientific, Waltham, Mass.). After filtration, an aliquot of up to 100 μL of the preserved specimen is removed for lung cancer detection test analysis. First, sputum cells are stained with hematoxylin (Electron Microscopy Sciences, Hatfield, Pa.) for downstream lung cancer detection test imaging. Cells are then treated with an antibody cocktail containing fluorescent conjugates chosen to both enrich for bronchial epithelial cells and to deplete contaminating inflammatory cells (neutrophils and macrophages). An anti-cytokeratin-FITC conjugate cocktail (Cell Signaling, Danvers, Mass.) targets cytokeratins expressed in both normal and malignant epithelial cells. An Anti-CD45-APC conjugate (Myltenti, Bergisch Gladbach, Germany) targets inflammatory cells for negative selection. Cells are also stained with DAPI (Life Technologies, Grand Island, N.Y.) prior to cell sorting. For FACS enrichment, a DAPI-positive mother gate is created to exclude doublet cells and debris, followed by exclusion of high side-scatter events, which are primarily oral squamous cells. Subsequently, a cytokeratin-high (High FITC) and CD45-Low (Low APC) daughter gate is drawn. The population of cells in this daughter gate are the enriched target epithelial cells sorted for a more efficient and downstream lung cancer detection test analysis using an optical tomography system such as the Cell-CT® optical tomography system.

Embedding of Enriched Cells

Following FACS enrichment, cells are dehydrated in ethanol followed by suspension in xylene. The cells are then transferred to and embedded in a suitable volume of the optical medium. The optical medium is a viscous oil with matching refractive index for the optical tomography system. Once embedded, cells are injected into a disposable cartridge for imaging on the optical tomography system.

Figure 2:
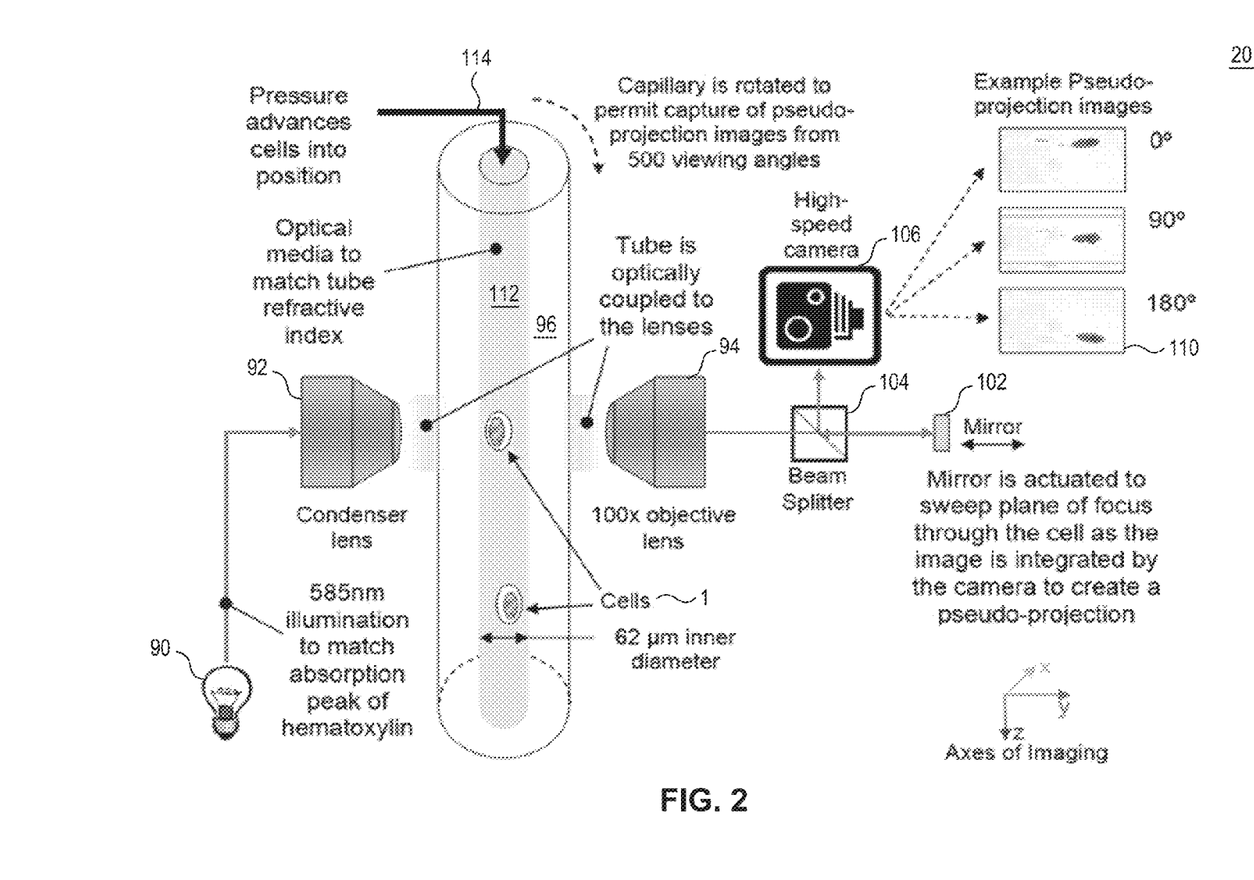
FIG. 2 schematically shows basic system components of a 3D optical tomography imaging system used in a lung cancer test system.

Referring now to FIG. 2, basic system components of a 3D optical tomography imaging system used in a lung cancer test system. The cell imaging system 20 is an automated, high-resolution 3D tomographic microscope and computing system for imaging cells in flow. Included are an illumination source 90 optically coupled to a condenser lens 92 which optically cooperates with an objective lens 94 for scanning images of objects 1 contained in a capillary tube 96. Images are obtained by scanning the volume occupied by the object by an oscillating mirror 102 and transmitted through a beam-splitter 104 to a high-speed camera 106. The high speed camera produces a plurality of pseudo-projection images 110. A set of pseudo-projection images for numerous axial tube rotation positions is produced for each object.

Although the test system is not limited to any one contrast method, in one example the lung cancer detection test specifically targets cell morphology based on the traditionally used hematoxylin stain. In the lung cancer detection test application, the optical tomography system computes 3D cell images with equal resolution in all dimensions (i.e. isotropic resolution) allowing measurements to be independent of orientation. Further, eliminating the focal plane ambiguity and view orientation dependencies typical of conventional microscopy provides information content to automatically recognize a broad spectrum of cell types, and unambiguously identify rare abnormal cells in a predominantly normal cell population. The optical tomography system output identifies about 0.5% of all cells as abnormal candidates to be verified using the CellGazer™ (VisionGate, Phoenix, Ariz.) workstation, an imaging software tool that allows human review of images free of focal plane and orientation ambiguity.

Optical tomography system imaging is performed on a small-volume liquid suspension. For lung cancer detection testing these cells are from the enriched epithelial cell population noted above. Because the optical tomography system can separate closely coincident objects, a narrowly focused core of single file cell flow, although a requirement in standard flow cytometry, is unnecessary.

The operation of examples of lung cancer test systems are described in the Nelson and Fauver references incorporated by reference hereinabove as well as other patents including U.S. Pat. No. 8,254,023 to Watson et al., issued Aug. 28, 2012 and entitled, "Optical Tomography System With High-Speed Scanner," which is also incorporated herein by reference. In operation stained nuclei of a biological cell 1 are suspended an optical media 112 and injected into a capillary tube 96 having, for example, a 62 μm inner diameter. The capillary system has been designed to be disposable, thus eliminating the possibility of cross-contamination between specimens. Pressure 114 is applied to the fluid moves objects 1 into position for imaging, before 3D data is collected as the tube rotates. A mirror 102 is actuated to sweep the plane of focus through the object, and the image is integrated by the camera to create a pseudo-projection from each single perspective[24]. Not shown is the glass holder that interfaces the capillary tube 96 to the optical tomography system. The holder has a hole cut through the middle that is slightly larger than the outside diameter of the capillary and glass flats on either side to allow optical coupling to the objective and condenser lenses. A capillary tube that is loaded with cells embedded in transport medium is threaded through the holder. The transport media that holds the cells, the glass capillary, capillary holder, oil to interface to the lenses and the lenses themselves are made from materials of the same optical index. As a consequence, rays of light pass through the optical tomography system optics, capillary and cells without refraction while the cell may be rotated to allow capture of a set of 500 pseudo-projections is taken as the capillary rotates through 360 degrees. Because the cells are suspended in a fluid medium, they are prone to a small amount of movement while pseudo-projection images 110 are collected.

Figure 3A:
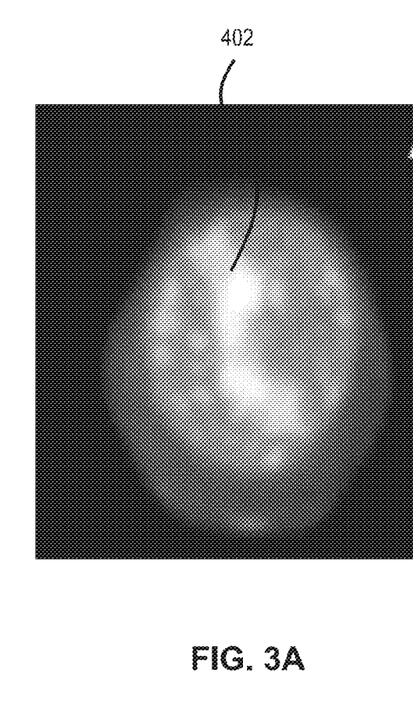
FIG. 3A-FIG. 3O show single perspective views of a 3D image of an adenocarcinoma cell.
Figure 3B:
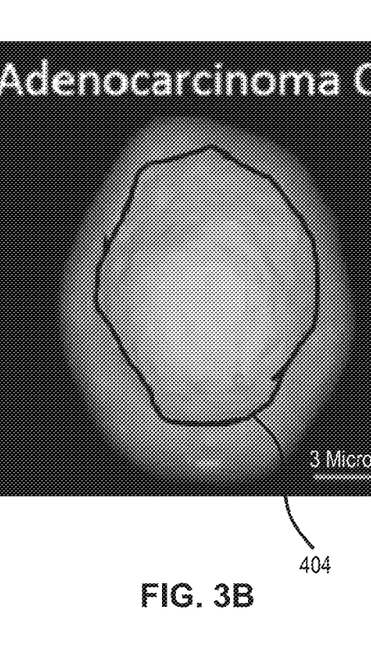
Figure 3C:
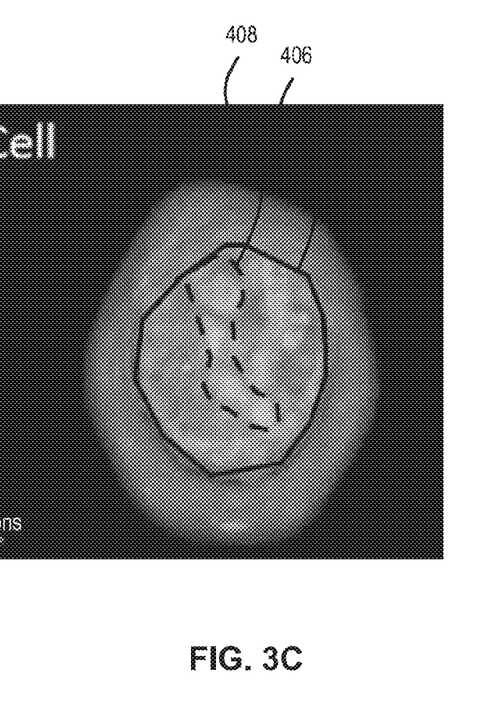

Cell images in the pseudo-projections, therefore, must be registered to a common center so that the cell features reinforce one another during the reconstruction. U.S. Pat. No. 7,835,561, issued Nov. 16, 2010 to Meyer et al. and entitled "Method for Image Processing and Reconstruction of Images for Optical Tomography," discloses error correction techniques for pseudo-projections. U.S. Pat. No. 7,835,561, is hereby incorporated by reference. The set of corrected pseudo-projections is processed using a filtered back-projection algorithm, similar to that in use in conventional X-ray CT, to compute the tomographic 3D cell reconstruction[13]. Pseudo-projections images 110 taken at three angular positions: 0 g, 90 g and 180 g are shown. Illumination is provided by a light source 90 at 585 nm wavelength to optimize image contrast based on the hematoxylin absorption spectrum. In the reconstruction, 3D pixels or voxels are cubic, with a size of 70 nm in each dimension. Reconstruction volumes vary in size, as the image collection volume is cropped around the object. Typically, volumes are approximately 200-300 pixels on the side. Referring now to FIG. 3A-FIG. 3C perspective views of a 3D image of an adenocarcinoma cell are shown. FIG. 3A shows the adenocarcinoma cell in maximum intensity projection[13]. Since grey values in the 3D image are associated with various cell features a look-up table that maps cell structures to color and opacity values was established to produce the cell image at center (as shown in FIG. 3B) and right (as shown in FIG. 3C). In color reproductions of these images, the cytoplasm is represented in translucent white 402, the nucleus in opaque blue 404, the loose chromatin and nucleoplasm in translucent green 406 and the condensed chromatin, and nucleoli are represented in opaque red 408. Given the strictures on international patent regulations to provide only black and white drawings these colors have been identified by borders identified by the corresponding reference numbers 404, 406 and 408 (shown as a broken line border).

Figure 4:
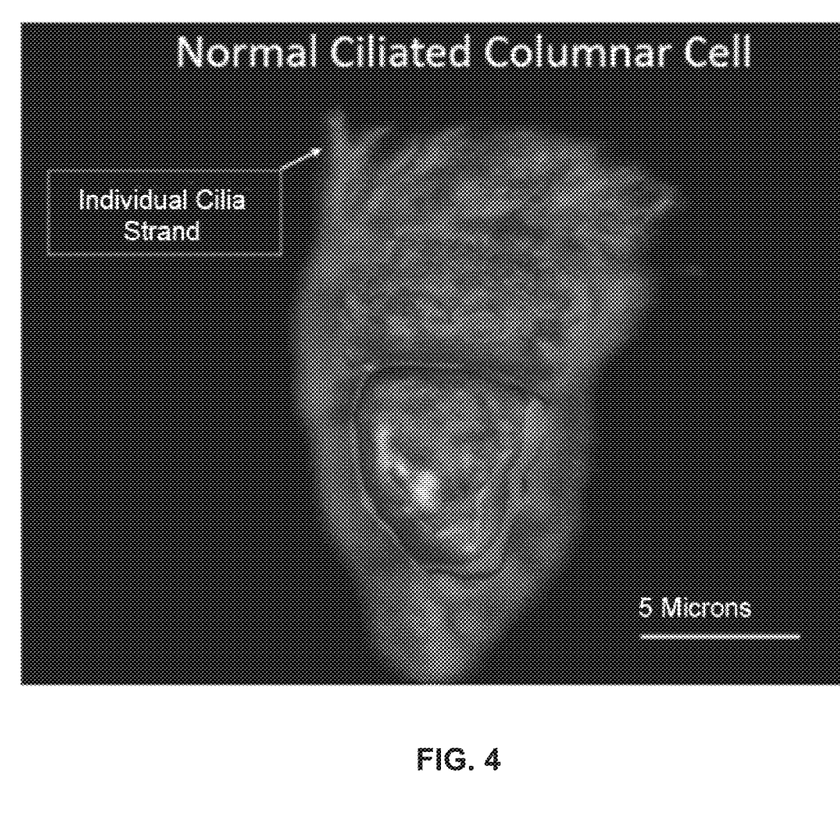
FIG. 4 shows cilia on lung columnar cell.

Referring now to FIG. 4, cilia on a lung columnar cell are shown. An imaged normal bronchial epithelial cell showing individual cilia strands measuring about 250 nm in diameter. This further demonstrates the resolution of the 3D cell imaging system.

Cell Classification

Figure 5:
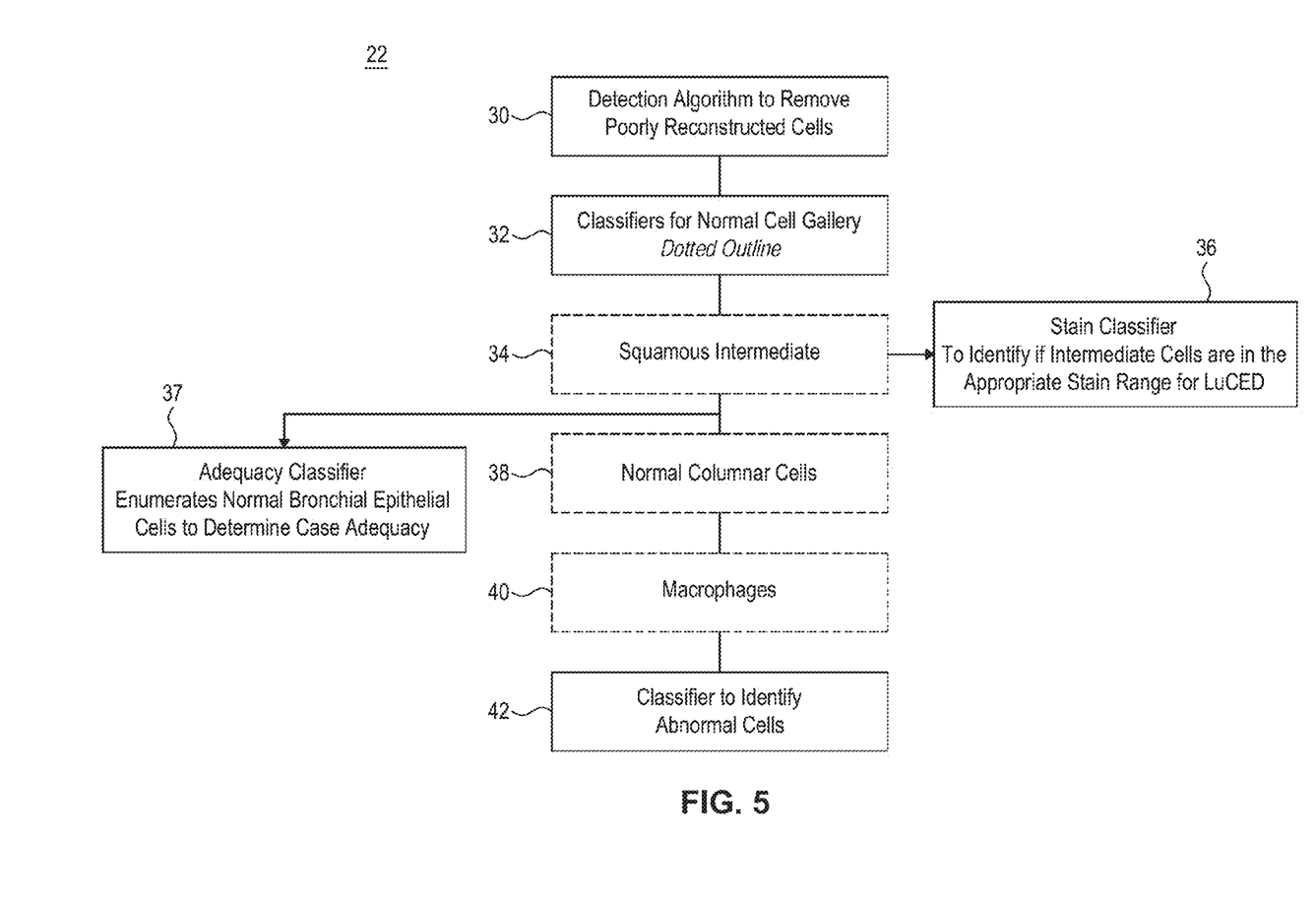
FIG. 5 schematically shows a functional block diagram of a lung cancer test for analysis of a sputum sample including an adequacy classifier.

Referring now to FIG. 5, a functional block diagram of a lung cancer test for analysis of a sputum sample including an adequacy classifier is schematically shown. Several cell classification algorithms are included. One advantage of the optical tomography system technology arises from automated 3D cell analysis, which can detect cell features that are too subtle or too complex for human reviewers. Automated classification eliminates highly variable human review of specimens. Moreover, classification based on 3D images overcomes inherent limitations associated with classification based on standard 2D, fixed focal plane images, as the 2D slice may not carry the essential image information to comprehensively identify the cell disease state[14]. Cell classification has the potential to automatically identify a few rare abnormal cells from the thousands of normal cells that are processed by the lung cancer detection test.

The classification steps for 3D cell classification 22 include a classifier to detect poor reconstructions 30, classifiers for a normal cell gallery 32, a stain classifier 36, an adequacy classifier 37 and an abnormal cell classifier 42. The classifiers used in the cytological detection system are trained as described below. In one useful example, the classifier to detect poor reconstructions 30 may be as described hereinabove with reference to Meyer et al. In one example, classifiers for a normal cell gallery 32 identify normal cells to serve as a reference point for human identification of abnormal cells using a review station. There are three classifiers that identify these normal cell types: normal squamous intermediate cells 34, normal columnar epithelial cells 38, and normal macrophages 40.

The stain classifier 36 operates, for example, by processing cells identified as squamous intermediate cells. The nucleus of a squamous intermediate cell has constant ploidy, making its overall integrated greyscale optical density value an ideal feature that can be used to assess whether specimen staining is in the correct range for optimal absorption contrast. Average and median grey scale values may be computed for each nuclei and a running average maintained. The stable value for the average is the stain that may be used as normalization for the individual grey scale values of the nucleus under consideration.

The adequacy classifier 37 enumerates reference cells, including, for example, normal bronchial epithelial cells and is used to determine if the processing of the specimen is adequate based on overall cell numbers. The adequacy classifier is described in more detail hereinbelow.

The abnormal cell classifier is generated by being trained to identify target cells having abnormal characteristics using classifier training methods described herein. These target cells (typically 0.5% of all cells processed) go on to be examined by a pathologist using the review station 25, such as a CellGazer™ workstation as developed by VisionGate, Inc. of Phoenix, Ariz. In certain embodiments target cells include abnormal squamous cells, adenocarcinoma cells, bronchioloalveolar carcinoma cells, abnormal neuroendocrine cells, small cell carcinoma cells, large cell carcinoma cells, lung columnar cells, tumor cells, neoplastic cells and bronchioloalveolar carcinoma cells and other cells and objects found in sputum.

Classifier Training—Inputs and Methods

Creation and optimization of the cell detection classifiers described above is generally referred to as "classifier training," as the process aims to accurately diagnose cells according to a reference or ground truth. There are two main aspects to accuracy: first is specificity (normal cells being called normal by the classifier), and second is sensitivity (abnormal cells being called abnormal by the classifier). Algorithm training methods include Adaptively Boosted Logistic Regression[18] and Random Forest[19]. Those skilled in the art will be familiar with how to apply other classical training techniques for classifiers such as template methods, adaptive processing and the like.

The methods used to train the classifier ensure an extremely good outcome given the data used as input. Primarily, classifier accuracy is ensured when the inputs to the classifier training process accurately describe clinically relevant aspects of the cells and are robust to environmental factors that could influence optical tomography system results:

1. As shown above with reference to FIG. 3A-FIG. 3C, three-dimensional cell images generated by the optical tomography system have high resolution, allowing precise measurements of critical features that support correct classification.
2. Some features that are useful in classification emerge only in the 3D image[17]. Consequently, the 3D feature set is not only more descriptive of the cell but also richer making classification based on three-dimensional imaging more accurate versus 2D imaging[16].
3. Three-dimensional, image segmentation algorithms have been developed to isolate the whole cell from the background and the nucleus from the cell. The accuracy of these segmentation algorithms was verified by comparing the segmented trace with human derived cell or nuclear envelope traces.
4. Feature measurements describe various aspects of the cell, cell nucleus, cytoplasm and cell nucleoli. In one example of a test system, 594 features are computed for each 3D cell image that represent object shape, volume, distribution of chromatin, and other, more subtle morphometric elements. Computation of these features has been verified to be independent of the orientation of the cell.
5. Diagnostic truth (the gold standard of pathology) for the classifier training is based on hierarchical cell diagnoses provided by two cytotechnologists and a cytopathologist. Users of a CellGazer™ workstation, for example, must first complete a training and testing program that emphasizes performance on cells that have been adjudicated to be normal or abnormal.

Classifier Training—Statistical Considerations

Secondarily, in one test carried out by the inventors herein, accuracy of the classifier training process was ensured through a rigorous process that encompassed three aspects:

1. The database that was used to train the classifier was formulated to contain sufficient material to ensure that binomial 95% confidence intervals[21] maintain variance of performance estimates within acceptable bounds.
2. Over-training is one potential pitfall of the training process where too much information could be included into the classifier so that the result could become over-specialized to the data used in the training. This situation generates an overly optimistic estimate for classifier performance. The risks of over-training can be mitigated through cross-validation[20] which involves taking a portion of the training data and using it as testing data. Limits for the amount of information that can be used in the classifier are reached when performance estimates based on training data exceed the estimates from testing data
3. Finally, as further assurance against over-training, the classifier was tested on data from a second set of cells that were not a part of the training process.

Abnormal Cell Classifier Training Summary

The following considerations were used to define the parameters governing the training for the abnormal cell classifier 42:

1. Since abnormal cells in sputum samples are scarce, and non-diagnostic elements in sputum are plentiful the classifier must operate with high sensitivity and very high specificity. As described later in Table 4, high case detection sensitivity is maintained when the single cell classifier sensitivity is 75% and the specimen contains more than one abnormal cell.
2. To ensure workload is maintained within reasonable limits, the goal for specificity was set at 99%.
3. Intervals for the lower binomial 95% confidence bound [21] were to be maintained within 70% for sensitivity and within 98.5% for specificity.

Based on these considerations, the training required at least 325 abnormal cells and 2,500 normal objects. Table 1 gives the cell counts used to train the abnormal cell classifier and shows the above requirements were met.

TABLE 1

| Cell Type | Numbers of Cells Used in Training |
| --- | --- |
| Abnormal | 554 |
| Normal | 23,626 |

Figure 6:
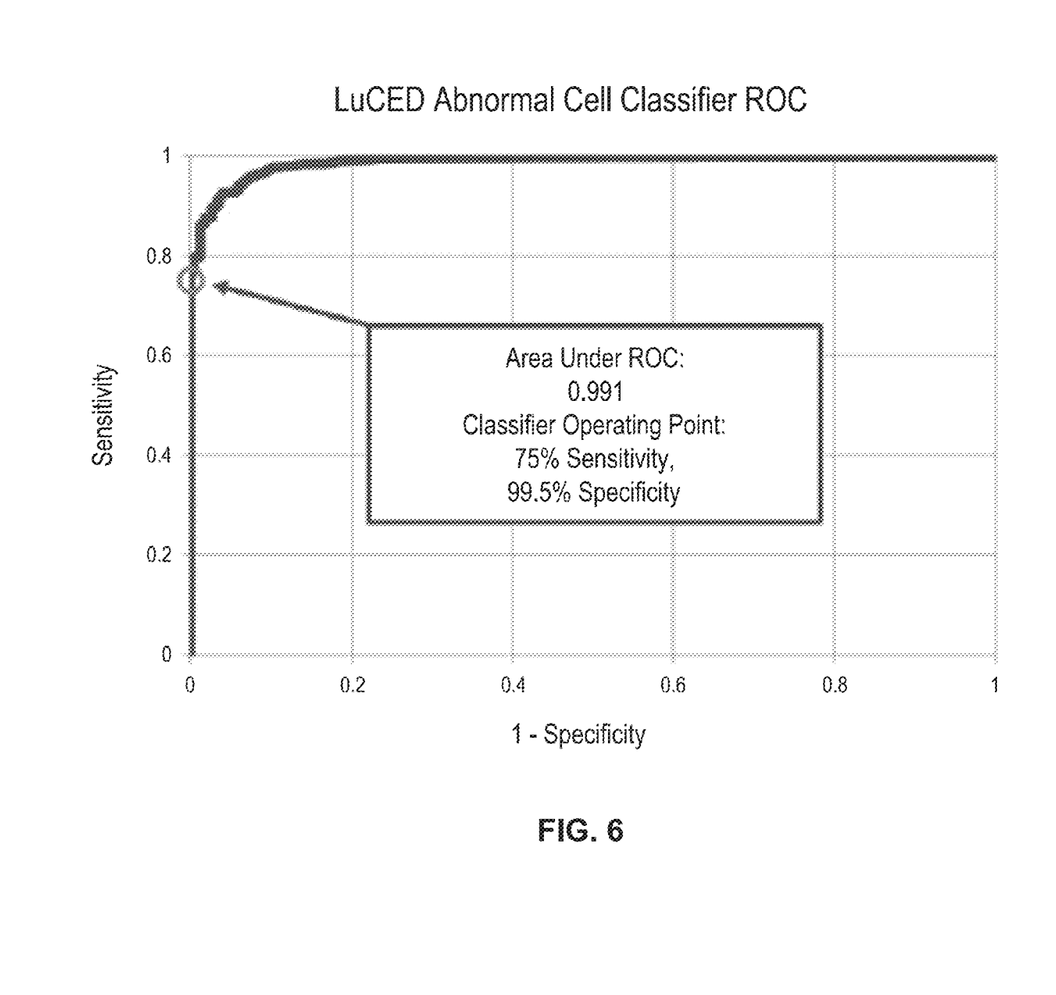
FIG. 6 shows an ROC curve for an abnormal cell classifier.

The lung cancer detection test Receiver Operator Characteristic (ROC) curve in FIG. 6 shows that lung cancer detection test meets performance objectives. Moreover, the numbers of samples in the training set indicated in Table 1 supports this classification performance within a very narrow binomial 95% confidence interval. Table 2 shows that sensitivity and specificity of lung cancer detection test with confidence intervals[21] meets the minimum intended goal.

TABLE 2

| Performance Category | Measured Value (%) | 95% Confidence Interval (%) | Goal for lower 95% confidence bound (%) |
| --- | --- | --- | --- |
| Single Cell Sensitivity | 75 | 71-79 | 70 |
| Single Cell Specificity | 100 | 99.5-99.6 | 98.5 |

The performance shown in Table 2 has also been verified using cells that were not included in the classifier training. Table 3 shows that performance projections based on training generalized to the cell population at large.

TABLE 3

| Performance Category | Cell Type | Number of Cells | 95% Confidence Interval (%) |
| --- | --- | --- | --- |
| Sensitivity | A549 | 26,717 | 86.0-86.8 |
| Specificity | Cells from sputum collected from normal patients | 35,419 | 99.5-99.7 |

Note that in Table 3, that the A549 (American Type Culture Collection, Manassas, Va.) cell line was used to test the classifier sensitivity. A549 is a cell line generated from a lung adenocarcinoma. As noted in Table 6 below, lung cancer detection test is trained to identify many different abnormal cell types. Adenocarcinoma and squamous cancer cells (including A549 cells) have the most distinctive features and are identified at a greater rate than the baseline 75% shown in Table 2.

In the end, a high detection rate is desired for each positive case. Sensitivity of single cell detection translates to detection of the abnormal case as shown in Table 4.

TABLE 4

| Number of Abnormal Cells in the analysis | Case sensitivity based on 71% individual cell sensitivity (%) |
| --- | --- |
| 1 | 71.0 |
| 2 | 91.6 |
| 3 | 97.6 |

One example of the lung cancer detection test abnormal classifier built by VisionGate, Inc. operates with an individual cell sensitivity of 75% at 99.5% specificity. The lower 95% binomial confidence bound for sensitivity indicated by Table 2 is 71%. Assuming independence of cell analysis, case sensitivity may be computed based on the probability of detecting any one cell and the knowledge of the number of abnormal cells that appear in the analysis. Independence is a good assumption since the optical tomography system processes cells one-at-a-time. Alternatively, factors relating to specimen processing or the fact that cells are from the same part of the lesion might influence scoring of the cells from a case. As a conservative measure against an overly optimistic estimate of case detection performance based on cell detection sensitivity, the inventors have estimated case detection sensitivity using the lower 95% confidence bound for individual cell detection sensitivity. Using this conservative figure, the case detection sensitivity can be estimated based on the number of abnormal cells encountered during the analysis. For example, if only one abnormal cell was encountered, the lower limit of case sensitivity would be 71%. If two abnormal cells were encountered the case sensitivity would be $100\%*(1-0.29*0.29)=91.6\%$. This trend of case detection vs. number of abnormal cells encountered is shown in Table 4.

The implications of Table 2, Table 3, and Table 4 are important for the lung cancer detection test. Results shown in these tables indicate that if an abnormal cell is in the group analyzed by the lung cancer detection test, it will be confidently detected so that the case will be identified with high sensitivity. This leaves the question of abnormal cell presence in the lung cancer detection test analysis as the remaining factor determining the cancer detection rate.

Specimen Adequacy

Because sputum is a highly variable specimen from patient to patient, a process is needed to evaluate whether the cells analyzed by lung cancer detection test comprise sufficient lung sampling for disease detection. Classical sputum adequacy is assessed based on the presence of abundant alveolar macrophages[22], however, these cell types are not preserved through the lung cancer detection test cell enrichment process. Furthermore, prior evaluations of the relationship between macrophage presence and abnormal cell presence in sputum have not given confidence in this adequacy determination method. Consequently, lung cancer detection test adequacy is based on an enumeration of reference cells, such as normal bronchial epithelial cells including metaplastic cells and columnar cells. As noted above, lung cancer detection test automatically enumerates these cells so that a separate manual analysis for adequacy is not required. As noted, lung cancer detection test specimen processing removes non-diagnostic elements in the sputum. This processing has the effect of randomizing the cellular content within the enriched cell pellet. This implies that the likelihood of encountering an abnormal cell during lung cancer detection test analysis of a specimen from a cancer patient depends primarily on the ratio of abnormal cells with the number of normal cells in the sample and the number of normal cells processed by lung cancer detection test. This ratio depends on many factors including the lesion size, dynamics of the cough, etc. Case detection then becomes primarily dependent on processing enough normal bronchial epithelial cells so that the abnormal cells are also processed.

Figure 7:
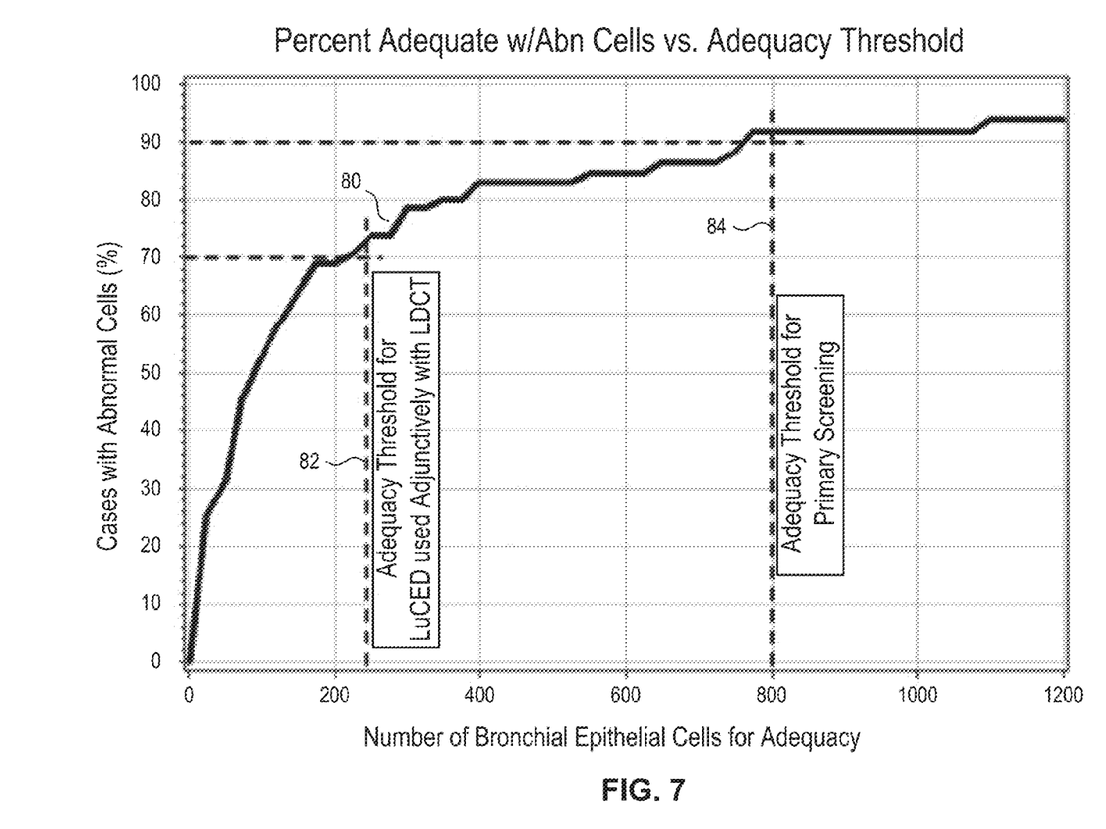
FIG. 7 graphically shows a curve plotting cases with abnormal cells against a number of normal bronchial epithelial cells for adequacy.

Referring now to FIG. 7, a curve plotting cases with abnormal cells against a number of bronchial epithelial cells for adequacy is graphically shown. Curve 80 represents the relationship between the percent of cases with abnormal cells on the vertical Y axis compared with the number of bronchial epithelial cells on the horizontal X axis. A first adequacy threshold 82 corresponds to 250 bronchial epithelial cells. A second adequacy threshold 84 corresponds to 800 bronchial epithelial cells. Classification of the abnormal cell cases is determined by the abnormal cell classifier 42. Note that the trend of curve 80 is valid for specimens produced through spontaneous coughs. Since induction changes cough dynamics, a different curve would likely need to be created for specimens collected through induction.

Use of the lung cancer detection test described herein depends on how the test is integrated with clinical practice. There are two modes: primary screener and adjunct with LDCT. In primary screening mode, lung cancer detection test is used as a first line screener with the goal of detecting lung cancer before it advances to an invasive condition. In this mode, the lung cancer detection test sensitivity is set to be greater than 90 percent[23]. Referring to the graph in FIG. 7, this level of sensitivity happens when lung cancer detection test has processed 800 normal bronchial epithelial cells. Thus, for primary screening, 800 is the required number of normal bronchial epithelial cells for adequacy. In adjunct mode, the lung cancer detection test follows LDCT to determine which positive cases from LDCT truly have abnormal cells, a lower lung cancer detection test sensitivity of 70% is acceptable, since the clinician would be availed of two orthogonal screening results. As indicated by threshold 82, lung cancer detection test sensitivity of 70% could be achieved when 250 normal bronchial epithelial cells have been identified.

To summarize, the lung cancer detection test has two modes of operation with the conditions for adequacy and the expected case sensitivity given in Table 5.

TABLE 5

| lung cancer detection test Mode | Number of normal bronchial epithelial cells required for adequacy | Expected lung cancer detection test sensitivity (%) |
| --- | --- | --- |
| Primary Screening | 800 | >90 |
| Adjunctive use with x-ray CT | 250 | >70 |

After reaching the adequacy criterion with no identification of any abnormal cells, the test may be safely terminated and the case called normal. Note that discovery of an abnormal cell by lung cancer detection test obviates considerations of adequacy. In this case, an abnormal result is reported by lung cancer detection test.

Classifier Development and Features

Generally, features are computed to provide numerical representation of various aspects of the 3D tomogram. The computed features are used along with expert diagnosis of the objects to develop a classifier that can distinguish between object types. For example, a data set with M 3D tomograms computed for objects of a first type, type 1, and N 3D tomograms may be computed for objects of a second type, type 2, such as normal and abnormal cells. Here "M" and "N" represent the number of type 1 and type 2 values respectively. The data set is preferably generated by an optical tomography system. The optical tomography system provides 3D tomograms including 3D images of objects such as, for example, a cell. A cell typically includes other features such as a nucleus having organelles such as nucleoli. Object types may include differing types of cells, organelles, cells exhibiting selected disease states, probes, normal cells or other features of interest. A set of x 3D image features are computed based on 3D tomograms for all M+N objects. Next a refined feature set of y 3D image features that best discriminate the object types is found, where "x" and "y" represent the number of 3D image features at each stage. The refined 3D image feature set of y 3D image features is used to build a classifier whose output correlates with the object type. In one example embodiment, at stage 102 a set of 3D tomograms is assembled, where the assembled set represent substantially all important markers that would be used by an expert to distinguish 3D biological object types. Having assembled a representative set of 3D tomograms, a 3D image feature set may be computed for each object that characterizes the important markers.

Features

Tomograms of biological objects, such as cells, exhibit a plurality of observable and measurable characteristics, some of which may be used as features for classification. Table 6 below provides a capsule summary of features, that is, important markers used to foster classification aims.

TABLE 6

FEATURES

| Feature Name | Brief Description |
| --- | --- |
| Volume | Number of connected voxels that comprise an object. |
| Surface Area | Number of voxels on the outer surface of a discrete object. |
| Shape features | Based on bounding box, surface area/volume ratio. |
| Location | Geometric center and center of mass of an object. |
| Voids | Based on a threshold T, number, volume, surface area, shape and location of inter-nuclear voids. |
| Invaginations | Based on a threshold T, count, size and location of nuclear invaginations. |
| Invagination Voids | Based on a threshold T, volume, surface area, shape, location of voids connected to invaginations. |
| Nucleoli | Based on a threshold T, volume, surface area, and shape, and location of objects likely to be nucleoli or chromatin condensations. |
| Nuclear texture features | The technique of a blur residue, using various sized structure elements, is used to separate various sized features within the nucleus. Overall 3D volume is then computed as are the number of discrete components, the volume histogram, average volume and variance, and shape histogram. |
| Distance metrics | Metrics describe spatial relationships between nucleoli, invaginations, voids, and the nuclear envelope. For example if three nucleoli are found the mean and variance, minimum and maximum inter-nucleoli distance may be found. Also the distance between the average coordinates for the cluster of the nucleoli and the center of mass for the entire object maybe found. Similar calculations may be formed by substituting any of the above entities for the nucleoli and the nuclear center of mass. |
| FFT features | FFT of a 3D tomogram and FFT features characterize prominent and average FFT characteristics. |
| Histogram statistical features | Statistical features related to the 3D histogram of grey values for voxels such as kurtosis, the statistical moment of Two dimensional features include texture |
| 2D features | features such as blur residue and geometric features including perimeter and circularity of the object. |

By way of further explanation, in one useful example, voids occurring in 3D biological objects have now been found to be useful classification features based on measurement criteria including comparison with a calculated or selected threshold. Another characteristic related to voids may include the number of voids in an object. Another characteristic related to voids includes volume of a void or number of voids. Yet another characteristic includes surface area of a void or number of voids. Shape and location of inter-nuclear voids may also be employed as a useful feature characteristic. Additionally combinations of feature characteristics may also be used to build a classifier as described hereinabove.

Similarly, invaginations occurring in 3D biological objects have now been found to be useful classification features based on measurement criteria including comparison with a calculated or selected threshold. Another characteristic related to invaginations may include the number of invaginations in an object. Another characteristic related to invaginations includes volume of an invaginations or number of invaginations. Yet another characteristic includes size of an invagination or number of invaginations. Location of nuclear invaginations also comprises a useful feature characteristic. Additionally, combinations of feature characteristics may also be used to build a classifier as described hereinabove.

Invagination voids occurring in 3D biological objects have now been found to be useful classification features based on measurement criteria including comparison with a calculated or selected threshold. Volume of invagination voids, surface area, shape, location of voids connected to invaginations and combinations of invagination features may also be advantageously used to build a classifier as described hereinabove.

Nucleoli occurring in 3D biological objects have now been found to be useful classification features based on measurement criteria including comparison with a calculated or selected threshold. Volume, surface area, shape, location of objects likely to be nucleoli or chromatin condensations and combinations of the aforesaid characteristics may also be advantageously used to build a classifier as described hereinabove. Nuclear texture features occurring in 3D biological objects have now been found to be useful classification features. Using various sized structure elements the technique of blur residue is used to separate various sized features within the nucleus. Blur residue techniques typically require blurring an image using a filter and measuring the resultant blur residue by applying marking operations. Overall 3D volume is then computed as are the number of discrete components, the volume histogram, average volume and variance, and shape histogram.

Distance metrics that describe spatial relationships between nucleoli, invaginations, voids, and the nuclear envelope have now been found to be useful classification features. For example, if three nucleoli are found the mean and variance, minimum and maximum inter-nucleoli distance may be found. Also the distance between the average coordinates for the cluster of the nucleoli and the center of mass for the entire object may be found. Similar calculations may be formed by substituting any of the above entities for the nucleoli and the nuclear center of mass.

Fast Fourier Transform (FFT) features now have also been found to be useful classification features. FFT features are formed by a Fast Fourier Transform of a 3D tomogram. The FFT features characterize prominent and average characteristics of the FFT classification.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated herein in their entirety by this reference.
1. Wilbur D C, Prey M U, Miller W M, Pawlick G F, Colgan T J. The AutoPap System for Primary Screening in Cervical Cytology: Comparing the Results of a Prospective, Intended-Use Study with Routine Manual Practice. Acta Cytol 1998; 42:214-20.
2. Wilbur D C, Black-Schaffer W S, Luff R D, Abraham K P, Kemper C, Molina J T, Tench W D. The Becton Dickinson FocalPoint G S Imaging System Clinical Trials Demonstrate Significantly Improved Sensitivity for the Detection of Important Cervical Lesions. Am J Clin Pathol 2009; 132:767-75.
3. Meyer M, Hayenga J, Neumann T, Katdare R, Presley C, Steinhauer D, Bell T, Lancaster C, Nelson A C. The Cell-C T 3D Cell Imaging Technology Platform Enables the Detection of Lung Cancer Using the Non-Invasive LuCED Sputum Test. (submitted Ca Cytopathol)
4. American Cancer Society. Cancer Facts and Figures 2015. Atlanta, Ga.: American Cancer Society; 2015. Accessed at cancer.org/on Mar. 10, 2015.
5. Pilotti S, Rilke F, Gribaudi G, Ravasi G L. Sputum cytology for the diagnosis of carcinoma of the lung. Acta Cytol. 1982; 26:649-54.
6. Sing A, Freudenberg N, Kortsik C, Wertzel H, Klosa B, Hasse J. Comparison of the sensitivity of sputum and brush cytology in the diagnosis of lung carcinomas. Acta Cytol. 1997; 41:399-408.
7. Van Rensburg A, Neethling G S, Schubert P T, Koegelenberg C F N, Wright C A, Bollinger C T, Bernasconi M, Diacon A H. Impact of routine sputum cytology in a population at high risk for bronchial carcinoma. Int J Tuberc Lung Dis. 2014; 18:607-12.
Press release: National Coverage Determination (NCD) for Screening for Lung Cancer with Low Dose Computed Tomography (LDCT). Baltimore, Md.: Centers for Medicare and Medicaid Services; 2015. Accessed at cms.gov on Mar. 10, 2015.
8. RadiologyInfo.org. Lung Cancer Screening. Oakbrook, I L: Radiologic Society of North America/American College of Radiology; 2015. Accessed at radiolodyinfo.org on Mar. 10, 2015.
9. Moyer V A, on behalf of the U.S. Preventive Services Task Force. Screening for Lung Cancer: U.S. Preventive Services Task Force Recommendation Statement. Ann Intern Med. 2014; 160:330-8.
10. The National Lung Screening Trial Research Team. Reduced lung-cancer mortality with low dose computed tomographic scanning. N Engl J Med. 2011; 365:395-409
11. Bach P B, Mirkin J N, Oliver T K, Azzoli C G, Berry D A, Brawley O T, et al. Benefits and harms of C T screening for lung Cancer. A systematic review. JAMA. 2012; 307:2418-29
12. Deans, S. The Radon Transform and some of its applications. Malabar: Dover, 2007.

13. Raswiki. Maximum intensity projection (MIP). Retrieved from Radiopaedia.org: [Accessed Mar. 19, 2015]
14. Dartmouth. (2004). Cilia and Flagella. Retrieved from www.dartmouth.edu: URL dartmouth.edu [Accessed Mar. 19, 2015]
15. Meyer M, Fauver M, Rahn J R, Neumann T, Patten F, Seibel E, Nelson A. Automated cell analysis in 2D and 3D: A comparative study. Pattern Recognition, 2009; 42(1):141-146.
16. Meyer M, Patten F, Presley C, Neumann T, Nelson A. Three-Dimensional Cellular Morphometry: A New Horizon for Cytology and Cancer Detection. Journal of the American Society of Cytopathology, 2012; 1(1):6-7.
17. Schapire R, Freund Y. Boosting, foundations and algorithms. Cambridge: MIT press, 2012.
18. Breiman, L. Random Forests. Machine Learning, 2001; 45(1):5-32.
19. Geisser, S. Predictive Inference. New York: Chapman and Hall, 1993
20. Clopper C, Pearson E. The use of confidence fiducial limits illustrated in the case of the binomial. Biometrika, 1934; 26(4):404-413.
21. Mody, D. Retrieved from cap.org: [Accessed Mar. 19, 2015]
22. Meyer M, Katdare R, Presley C, Wilbur D, Neumann T, Hayenga J, et al. Early detection of lung cancer based on three-dimensional, morphometric analysis of cells from sputum. Journal of Clinical Oncology, 2014; 32:55.
23. Fauver M, Seibel E, Rahn J R, Meyer M, Patten F, Neumann T, Nelson A. Three-dimensional imaging of single isolated cell nuclei using optical projection tomography. Optics Express, 2005; 13(11):4210-4223.

What is claimed is:

1. A cytological analysis test for 3D cell classification from a specimen comprising:
   isolating and preserving at least one cell from the specimen;
   enriching the at least one cell;
   embedding the at least one enriched cell into an optical medium;
   injecting at least one embedded cell into a capillary tube;
   applying pressure to the at least one embedded cell until it appears in a field of view of a pseudo-projection viewing subsystem;
   acquiring at least one pseudo-projection image of at least embedded cell that is in the field of view using the pseudo-projection viewing subsystem;
   rotating the capillary tube about a tube axis to generate additional pseudo-projection images at different views using the pseudo-projection viewing subsystem to provide a set of pseudo-projection images for each embedded cell;
   reconstructing each embedded cell using data from the set of pseudo-projection images to produce a set of 3D cell reconstructions;
   operating a biological specimen classifier to detect reference cells, wherein the reference cells are identified and selected from the group comprising normal bronchial epithelial cells, metaplastic cells and columnar cells;
   enumerating the detected reference cells in the specimen;
   operating a second cell classifier with a predetermined single cell sensitivity value and predetermined single cell specificity value as characterized by a receiver operating curve (ROC) to detect target cells comprising abnormal lung cells; and
   operating an adequacy classifier to compare the number of reference cells against a threshold value of enumerated reference cells so as to determine specimen adequacy.

2. The method of claim 1 wherein the target cells are selected from the group consisting of abnormal squamous cells, adenocarcinoma cells, bronchioloalveolar carcinoma cells, abnormal neuroendocrine cells, small cell carcinoma cells, non-small cell carcinoma cells, lung columnar cells, tumor cells, neoplastic cells and bronchioloalveolar carcinoma cells and other cells and objects found in sputum.

3. The method of claim 1 wherein the threshold value is in a statistically predetermined range.

4. The method of claim 1 wherein the threshold value is in a range between 250 and 800 normal bronchial epithelial cells.

5. The method of claim 4 wherein adequacy classifier training is implemented using a feature measurement set descriptive of an object including three-dimensional image segmentation algorithms.

6. The method of claim 5 wherein the object is a cell with a nucleus and the three-dimensional image segmentation algorithms isolate the whole cell from the background and the nucleus from the cell.

7. The method of claim 5 wherein adequacy classifier training is implemented using a feature measurement set including features selected from the group consisting of cell nucleus, cytoplasm and cell nucleoli, object shape, volume, distribution of chromatin, and other morphometric elements.

8. The method of claim 1 further comprising generating the biological specimen classifier using the adequacy classifier training for specificity and sensitivity where sensitivity is relative to target cells and specificity is with respect to non-desired cells in the specimen.

9. The method of claim 1 further comprising generating the second cell classifier using classifier training for specificity and sensitivity.

10. The method of claim 9 wherein classifier training is implemented using features from abnormal cells and normal objects.

11. The method of claim 1 further comprising obtaining the specimen from a sputum specimen.

12. The method of claim 11 further comprising enriching the sputum specimen.

13. The method of claim 12 wherein enriching the sputum specimen comprises using fluorescence activated cell sorting or immuno-magnetic enrichment.

14. A method for implementing a test indicative of lung cancer for a patient comprising:
   obtaining a sputum specimen from the patient;
   isolating and preserving at least one cell from the specimen;
   enriching the at least one cell;
   embedding the at least one enriched cell into an optical medium;
   injecting at least one embedded cell into a capillary tube;
   applying pressure to the at least one embedded cell until it appears in a field of view of a pseudo-projection viewing subsystem;
   acquiring at least one pseudo-projection image of at least embedded cell that is in the field of view using the pseudo-projection viewing subsystem;
   rotating the capillary tube about a tube axis to generate additional pseudo-projection images at different views using the pseudo-projection viewing subsystem to provide a set of pseudo-projection images for each embedded cell;

reconstructing each embedded cell using data from the set of pseudo-projection images to produce a set of 3D cell reconstructions;

operating a biological specimen classifier to detect reference cells, wherein the reference cells are identified and selected from the group comprising normal bronchial epithelial cells, metaplastic cells and columnar cells;

enumerating the detected reference cells in the specimen;

operating a second cell classifier with a predetermined single cell sensitivity value and predetermined single cell specificity value as characterized by a receiver operating curve (ROC) to detect target cells comprising abnormal lung cells operating an adequacy classifier to compare the number of normal bronchial epithelial cells against a threshold value of enumerated normal bronchial epithelial cells; and if the threshold value is met or exceeded then proceeding to carry out further analysis of the set of 3D cell reconstructions.

15. The method of claim 14 further comprising subjecting the patient to low dose CT radiographic scanning.

16. The method of claim 14 wherein the threshold value is in a statistically predetermined range.

17. The method of claim 15 wherein the threshold value is in a range between 250 and 800 normal bronchial epithelial cells.

18. The method of claim 14 further comprising generating the biological specimen classifier using classifier training for specificity and sensitivity.

19. The method of claim 18 wherein classifier training is implemented using a feature measurement set descriptive of the cell including three-dimensional image segmentation algorithms that isolate the whole cell from the background and the nucleus from the cell.

20. The method of claim 18 wherein classifier training is implemented using a feature measurement set including features selected from the group consisting of cell nucleus, cytoplasm and cell nucleoli, object shape, volume, distribution of chromatin, and other morphometric elements.

21. The method of claim 18 wherein classifier training is implemented using features from abnormal cells and normal objects.

22. The method of claim 14 further comprising generating the abnormal cell classifier using classifier training for specificity and sensitivity.

23. The method of claim 14 further comprising obtaining the specimen from a sputum specimen.

24. The method of claim 14 further comprising enriching the sputum specimen.

25. The method of claim 24 wherein enriching the sputum specimen comprises using fluorescence activated cell sorting or immuno-magnetic enrichment.

26. The method of claim 14 wherein the target cells are selected from the group consisting of abnormal squamous cells, adenocarcinoma cells, bronchioloalveolar carcinoma cells, abnormal neuroendocrine cells, small cell carcinoma cells, large cell carcinoma cells, lung columnar cells, tumor cells, neoplastic cells and bronchioloalveolar carcinoma cells and other cells and objects found in sputum.

27. A cytological analysis test system for 3D cell classification from a specimen comprising:

means for isolating and preserving at least one cell from the specimen;

means for enriching the at least one cell;

means for embedding the at least one enriched cell into an optical medium;

means for injecting at least one embedded cell into a capillary tube;

means for applying pressure to the at least one embedded cell until it appears in a field of view of a pseudo-projection viewing subsystem;

means for acquiring at least one pseudo-projection image of at least embedded cell that is in the field of view using the pseudo-projection viewing subsystem;

means for rotating the capillary tube about a tube axis to generate additional pseudo-projection images at different views using the pseudo-projection viewing subsystem to provide a set of pseudo-projection images for each embedded cell;

means for reconstructing each embedded cell using data from the set of pseudo-projection images to produce a set of 3D cell reconstructions;

means for operating a biological specimen classifier to detect reference cells, wherein the reference cells are selected from the group comprising normal bronchial epithelial cells, metaplastic cells and columnar cells;

means for enumerating the detected reference cells in the specimen;

means for operating a second cell classifier with a predetermined single cell sensitivity value and predetermined single cell specificity value as characterized by a receiver operating curve (ROC) to detect target cells comprising abnormal lung cells; and means for operating an adequacy classifier to compare the number of reference cells against a threshold value of enumerated reference cells so as to determine specimen adequacy.

* * * * *